US008354257B2

(12) United States Patent
Datta et al.

(10) Patent No.: US 8,354,257 B2
(45) Date of Patent: Jan. 15, 2013

(54) INTEGRATED PROCESS FOR PRODUCTION OF ALCOHOL FROM SYNGAS AND REMOVAL OF $CO_2$

(75) Inventors: Rathin Datta, Warrenville, IL (US); Ralph Corley, Pensacola Beach, FL (US)

(73) Assignee: Coskata, Inc., Warrenville, IL (US)

( * ) Notice: Subject to any disclaimer, the term of this patent is extended or adjusted under 35 U.S.C. 154(b) by 363 days.

(21) Appl. No.: 12/684,695

(22) Filed: Jan. 8, 2010

(65) Prior Publication Data

US 2011/0171706 A1 Jul. 14, 2011

(51) Int. Cl.
*C12P 7/06* (2006.01)
(52) U.S. Cl. ......... 435/161; 435/160; 435/170; 435/171
(58) Field of Classification Search .................. 435/160, 435/161, 170, 171
See application file for complete search history.

(56) References Cited

U.S. PATENT DOCUMENTS

| | | | |
|---|---|---|---|
| 4,336,335 A | 6/1982 | Muller et al. | |
| 4,372,925 A * | 2/1983 | Cornelisse | 423/226 |
| 5,173,429 A | 12/1992 | Gaddy et al. | |
| 6,136,577 A | 10/2000 | Gaddy | |
| 6,340,581 B1 | 1/2002 | Gaddy | |
| 6,919,488 B2 | 7/2005 | Melnichuk et al. | |
| 7,118,672 B2 | 10/2006 | Husain et al. | |
| 7,285,402 B2 | 10/2007 | Gaddy et al. | |
| 2003/0211585 A1* | 11/2003 | Gaddy et al. | 435/161 |
| 2007/0275447 A1 | 11/2007 | Lewis et al. | |
| 2008/0057554 A1 | 3/2008 | Huhnke et al. | |
| 2008/0305539 A1 | 12/2008 | Hickey et al. | |
| 2009/0029434 A1 | 1/2009 | Tsai et al. | |
| 2009/0035848 A1 | 2/2009 | Hickey et al. | |
| 2009/0104676 A1 | 4/2009 | Tsai et al. | |
| 2009/0215139 A1 | 8/2009 | Datta et al. | |
| 2009/0215142 A1 | 8/2009 | Tsai et al. | |
| 2009/0215153 A1 | 8/2009 | Tsai et al. | |
| 2009/0215163 A1 | 8/2009 | Tsai et al. | |
| 2009/0286296 A1 | 11/2009 | Hickey et al. | |

FOREIGN PATENT DOCUMENTS

| | | |
|---|---|---|
| WO | 2007-117157 A1 | 10/2007 |
| WO | 2008-154301 A1 | 12/2008 |
| WO | WO2008154301 | 12/2008 |
| WO | 2009-105372 A1 | 8/2009 |
| WO | 2009-108503 A1 | 9/2009 |

OTHER PUBLICATIONS

U.S. Appl. No. 12/258,193, filed Oct. 24, 2008, Datta et al.
Clausen, E.C., et al., "Ethanol From Biomass by Gasification/Fermentation", Presented at Plastics, Tires, Auto Wastes/Biomass MSW Symposium, Fall 1993, Chicago, 38 (3).
Klasson, K.T., et al., "Biological Production of Liquid and Gaseous Fuels from Synthesis Gas," Appl. Biochem. Biotechnol., vol. 24-25, No. 1, Mar. 1990, 857-873.
Vega, J. L., et al., "The Biological Production of Ethanol from Synthesis Gas," Appl. Biochem. Biotechnol. vol. 20-21, No. 1, Jan. 1989, 781-797.
Phillips, John R., et al., "Synthesis Gas as Substrate for the Biological Production of Fuels and Chemicals," Appl. Biochem. Biotechnol. vol. 45-46, No. 1, Mar. 1994, 145-157.
Barik, S., et al., "Biological Production of Alcohols from Coal Through Indirect Liquefaction," Appl. Biochem. Biotechnol. vol. 18, No. 1, Aug. 1988, 363-387.
Henstra, A. et al., "Microbiology of synthesis gas fermentation for biofuel production," Current Opinion in Biotechnol., vol. 18, Mar. 2007, 200-206.
Abrini, J. et al., "Clostridium autoethanogenum, sp. nov., an anaerobic bacterium that produces ethanol from carbon monoxide," Arch. Microbiol. vol. 161, 1994, 345-351.
Das, A. and Ljungdahl, L.G., "Electron Transport System in Acetogens," Biochemistry and Physiology of Anaerobic Bacteria, 2003, 191-204, Springer-Verlag New York, Inc., New York, US.
Drake, H. and Kusel, K., "How the Diverse Physiologic Potentials of Acetogens Determine Their in Situ Realities," Biochemistry and Physiology of Anaerobic Bacteria, 2003, 171-190, Springer-Verlag New York, Inc., New York, US.
Grethlein, A. et al., "Evidence for Production of n-Butanol from Carbon Monoxide by Butyribacterium methlyotrophicum," J. Ferment. Bioeng., vol. 72, No. 1, 1991, 58-60.
Worden, R.M., et al., "Production of butanol and ethanol from synthesis gas via fermentation," Fuel. vol. 70, May 1991, 615-619.

* cited by examiner

*Primary Examiner* — Susan Hanley
*Assistant Examiner* — Nghi Nguyen (57) ABSTRACT

A process for producing alcohol from syngas integrates the alcohol recovery with the removal of $CO_2$ from syngas. A syngas feed containing CO, $H_2$, and $CO_2$ contacts an aqueous alcohol stream to remove $CO_2$ from the syngas that then passes to bioreactor containing microorganisms for conversion to alcohol and other liquid products. Flashing of the scrubbing liquid releases the $CO_2$ and simultaneously concentrates alcohol in the overhead flash vapor. Condensation of the flash vapor provides an enriched alcohol stream for enhanced recovery of the ethanol product in a product separation zone. The remainder of the scrubbing liquid along with make-up alcohol and water from the process gets returned for continued contact with the syngas feed.

22 Claims, 1 Drawing Sheet

INTEGRATED PROCESS FOR PRODUCTION OF ALCOHOL FROM SYNGAS AND REMOVAL OF $CO_2$

FIELD OF THE INVENTION

This invention relates to the production of alcohol and liquid products from syngas. More specifically this invention relates to the removal of $CO_2$ from syngas in a process for the production of alcohol from syngas.

DETAILED DESCRIPTION

Background

The production of alcohol by fermentation is of particular interest due to the increased emphasis on the conversion of renewable energy sources into liquid products. For example, conversion of biomass for biofuel production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses, and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

To break down these recalcitrant structures to provide fermentable sugars for bioconversion to ethanol typically requires pretreatment steps together with chemical/enzymatic hydrolysis. Processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol, or chemicals such as acetic acid, butyric acid and the like. This path can be inherently more efficient than the pretreatment/hydrolysis/fermentation path because the gasification step can convert all of the components to syngas with good efficiency (e.g., more than 75% of the energy can be available as fermentable compounds), and some strains of anaerobic microorganisms can convert syngas to ethanol, n-butanol, or other chemicals with high (e.g., greater than 90% of theoretical) efficiency.

Moreover, syngas can be made from many other carbonaceous feedstocks. These include sources of hydrocarbons such as natural gas, reformed gas, peat, petroleum coke, and coal. Other sources for production of syngas include waste material such as debris from construction and demolition, municipal solid waste, and landfill gas. Therefore generation and utilization of syngas can provide a more broad technology path to production of liquid products.

Effective use of this technology requires that the syngas components CO and $H_2$ be efficiently and economically dispersed or dissolved in the aqueous medium and transferred to anaerobic microorganisms that convert them to the desired products. And very large quantities of these gases are required. For example, in the case of ethanol production the theoretical equations for CO or $H_2$ and $CO_2$ to ethanol are:

$$6CO + 3H_2O \rightarrow C_2H_5OH + 4CO_2$$

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol produced. Other products such as acetic acid and n-butanol have similar large stochiometric requirements for these gases. As the first equation shows the presence of CO in this technology path will also produce $CO_2$. Since the process both receives $CO_2$ with the syngas and produces $CO_2$ as part of the conversion of CO into ethanol there is an excess of $CO_2$. Reducing this excess $CO_2$ by removing $CO_2$ can improve the process. Removing $CO_2$ from the syngas lowers the total mass flow of gas into the fermentation zone where the bioconversion takes place. In addition a high concentration of $CO_2$ can inhibit growth and productivity of the microorganisms in the fermentation zone.

Syngas derived from any gasification process—direct or indirect, typically has a molar concentration of $CO_2$ in a range between 10 and 20% on an anhydrous basis. Thus, there is a substantial amount of $CO_2$ present in the syngas, and reducing the amount of $CO_2$ in the syngas feed to a bioreactor will aid the fermentation step both in terms of mass flow and $CO_2$ concentration.

There are numerous commercial processes for $CO_2$ removal from gas streams. Such processes include amine extraction, alkaline salt extractions, water absorption, membrane separation, adsorptions/desorption, and physical absorption in organic solvents. These processes typically remove $CO_2$ to relatively low concentrations of less than 1 wt % and add considerable expense to the process. Methods are sought to remove $CO_2$ from the syngas with low capital expense and a good operating efficiency.

SUMMARY OF THE INVENTION

This invention is a method of absorbing $CO_2$ from a syngas stream used in the production of alcohol with an aqueous stream containing alcohol produced in the process and producing an enriched alcohol stream. Since $CO_2$ gets produced in the bioconversion of the syngas, the aqueous alcohol stream needs to effect only a partial reduction in the $CO_2$ concentration to provide the benefit of this invention. Therefore this invention recognized the benefit that utilization of alcohol and water, already present in such processes, can bring to the removal of $CO_2$ from the feed gas in the production of an enriched alcohol stream. Furthermore, achieving these benefits does not require a near complete removal of $CO_2$.

It is known that an alcohol-water mixture has a considerably higher solubility for $CO_2$ than water alone. In the case of ethanol at conditions of 1 bar g and 25° C. the solubility of $CO_2$ in ethanol alone is 0.6 mole %, an ethanol water mixture with 90 mole % ethanol has a solubility of 0.45 mole % and water by itself has a solubility of $CO_2$ equal to 0.05 mole %. At higher pressures of 4 bars g the $CO_2$ solubility in 90 mole % ethanol and water mixture is 2.5 mole %. This provides an effective absorption capacity when compared to commercially designed solvents. For example, propylene carbonate which is widely used for $CO_2$ removal has a capacity of 6.4 mole % $CO_2$ at 4 bars g and 25° C.

The other important property of the alcohol-water mixtures is a low solubility for CO and $H_2$. These solvents have two orders of magnitude higher solubility for $CO_2$ than for CO and $H_2$. Therefore, the use of such solvents will result in very low losses of the gases that are sought for primary conversion in the fermentation zone.

As compared to the more conventional processes, this process uses relatively low targets for $CO_2$ removal. $CO_2$ removal from this process is in the range of from 20 to 5 mole %. At these levels the process can use mild operating conditions in the $CO_2$ removal section. Such conditions will usually include temperatures in a range of from 25 to 40° C. and pressures of from atmospheric to 7 bars g and more typically from 3 to 7 bars g. Such conditions are quite compatible with the operating conditions of the typical syngas bioconversion processes.

In addition since the alcohol is the same as that produced in the process there is no need to remove all of the alcohol from the treated syngas. Thus, the treated syngas can be cooled to partially condense the alcohol or can pass directly from the contactor that removes the $CO_2$ to the fermentation zone. Volatile organic impurities that may be present in the syngas such as light aromatic or aliphatic hydrocarbons may get captured with the ethanol but will act as minor components of denaturants and fusel oils that are typically found in ethanol from fermentation.

The ready availability of alcohol and water mixtures and its use as the scrubbing liquid offers dramatic improvements in efficiency over the use of water alone. The volume of scrubbing liquid required to effect the removal of the $CO_2$ is reduced five fold by the use of a 50-50 mole percent water-alcohol mixture as compared to water alone. This reduction in scrubbing liquid volume combined with the need for only partial $CO_2$ removal allows this invention to provide a practical and low cost method for improving alcohol fermentation from syngas processes.

Furthermore, the process offers an added advantage of removing trace gases and impurities. Some of the trace impurities that are present in the syngas include sulfur containing impurities $H_2S$ and COS and the nitrogen containing impurities—$NH_3$ and HCN. These compounds will also be substantially removed during the $CO_2$ removal by scrubbing with aqueous alcohol, in particular ethanol. Furthermore, the $H_2S$ and COS will be desorbed just like the $CO_2$ and separate from the aqueous alcohol by desorption such as in a flash process step. The invention can be quite effective in also removing these trace compounds. For example, the solubility of $H_2S$ in water is approximately 3 fold higher than that of $CO_2$ at similar temperatures and pressures. In 50:50 mole % ethanol/water the $H_2S$ solubility is increased 2 fold compared to that in water alone. When the pressure is lowered or temperature is increased, the dissolved $H_2S$ is released just like the dissolved $CO_2$. Thus, scrubbing with the alcohol and water mixture will also remove minor impurities present in the syngas such as $H_2S$, COS, and other acid gases along with the $CO_2$.

In addition, treatment of the scrubbing liquid to release the $CO_2$ will also advantageously concentrate the alcohol in the $CO_2$ rich gas that gets desorbed from the scrubbing liquid. Therefore, the scrubbing section provides a $CO_2$ rich effluent gas from which a concentrated ethanol stream is readily condensed. In practice the process may employ a desorption step of flashing the $CO_2$ from the alcohol and water mixture of the scrubber liquid. This flashing will enrich the alcohol by separation of the vapor phase alcohol stream from the water. In the case of ethanol and depending on its concentration in the scrubber liquid the enriched ethanol may be anhydrous or close to anhydrous. Distillation zones or other separation sections can readily recover this ethanol after it is condensed out of the flashed gas so that the process operates without any significant loss of ethanol. In fact, concentration of ethanol in the recovered condensate may exceed 80 wt % thereby making it suitable for direct introduction into a rectification zone of a product recovery section.

Another aspect of this invention may add an alcohol enrichment step at other locations in the process. For example, a condensing section may receive the overhead stream from the contactor where the syngas initially contacts the aqueous ethanol stream. A condenser at this location can, using a minimal amount of refrigeration, recover a condensate with an ethanol concentration that exceeds 80%. This concentration again makes the condensate from the contactor overhead stream suitable for direct introduction into a rectification zone of the product recovery section.

More generally a contactor and flash vessel arrangement may find application at other locations in the process. For example tail gas stream from the bioreactors will have a high $CO_2$ and ethanol concentration. Contacting the tail gas with a low concentration ethanol stream can again provide overhead vapor stream from which a condenser can recover a stream containing ethanol at high concentration.

Such contactor arrangements may also find application in process arrangements that use stages of bioreactor contacting. For example, the syngas may, especially in the case of membrane type bioreactors, pass through a series of bioreactors. US 2008/0305539 A1 shows an arrangement of multiple stages of bioreactors with an intermediate step $CO_2$ between bioreactors using membrane separation. The present invention provides a more efficient method of intermediate $CO_2$ removal from the tail gas of the lead bioreactor as it passes to the downstream bioreactor. Passing the tail gas from a lead reactor to the contactor and flash vessel of this invention will remove $CO_2$ between reactor stages while also permitting recovery of a high concentration ethanol stream.

Accordingly in a broad form this invention is a process for the production of alcohol from a feed gas comprising $CO_2$ and at least one of hydrogen and CO. The process contacts, typically in a scrubbing vessel, a feed gas comprising $CO_2$ and at least one of hydrogen and CO with a first aqueous alcohol stream to absorb $CO_2$ from the feed gas and separate the contacted streams into a $CO_2$ reduced feed gas and a $CO_2$ enriched liquid stream. The $CO_2$ reduced feed gas passes to a bioreactor for contact therein with microorganisms that convert at least a portion of the hydrogen and $CO_2$, or CO to a bioreactor effluent stream comprising alcohol. The $CO_2$ enriched liquid stream is separated into a gaseous $CO_2$ effluent stream and a second aqueous alcohol stream. At least a portion of the second aqueous alcohol stream is returned to the first aqueous alcohol stream for contact with the feed gas. The process also recovers alcohol from the bioreactor effluent stream and introduces a portion of the alcohol from this stream into the first aqueous alcohol stream. The bioreactor usually produces a liquid product comprising at least one of ethanol or butanol. Typically the first aqueous alcohol stream will comprise from 30 to 70 mole % alcohol in water. The process may also separate the $CO_2$ effluent stream to produce a $CO_2$ off gas stream and an alcohol enriched stream and may separate the $CO_2$ reduced feed gas stream to produce a $CO_2$ feed off gas stream and a recovered alcohol containing stream. The feed gas off stream now contains the feed gas from the $CO_2$ reduced feed gas and passes to the bioreactor for contact with the microorganisms.

In a more limited form of this invention the process contacts a feed gas comprising $CO_2$ and at least one of hydrogen and CO with a first aqueous ethanol stream to absorb $CO_2$ from the feed gas and separates the contacted streams into a $CO_2$ reduced feed gas and a $CO_2$ enriched liquid stream. The $CO_2$ reduced feed gas passes to a bioreactor for contact therein with microorganisms that convert at least a portion of the hydrogen and $CO_2$, or CO to a bioreactor effluent stream comprising ethanol. The $CO_2$ enriched liquid stream is separated into a $CO_2$ effluent stream and a second aqueous ethanol stream. The recovery of ethanol from the $CO_2$ enriched stream produces a $CO_2$ off-gas stream and an ethanol enriched stream. At least a portion of the second aqueous ethanol stream may be returned to the first aqueous ethanol stream for contact with the feed gas. The process adds a portion of the bioreactor effluent stream and/or the ethanol enriched stream to supply make-up ethanol to the first aqueous ethanol stream.

In another more limited form of this invention the process passes the feed gas comprising $CO_2$, $H_2$, CO, COS and $H_2S$ and a first aqueous ethanol stream to a contactor wherein $CO_2$, COS and $H_2S$ from the feed gas are adsorbed to produce a $CO_2$ reduced feed gas and a $CO_2$ enriched stream. The $CO_2$ enriched stream also contains COS and $H_2S$. The $CO_2$ reduced feed gas passes to a bioreactor for contact therein with microorganisms that convert at least a portion of the hydrogen and $CO_2$, or CO into a bioreactor effluent stream comprising ethanol. Separation of ethanol from the $CO_2$ enriched stream in a separator produces a $CO_2$ effluent stream and a second aqueous ethanol stream. Condensing ethanol from the $CO_2$ effluent stream produces a $CO_2$ off gas stream and an ethanol enriched stream. At least a portion of the bioreactor effluent stream and the ethanol enriched stream passes to an ethanol recovery zone to produce an ethanol effluent stream having an ethanol concentration of at least 90 wt %. At least a portion of the second aqueous ethanol stream joins the first aqueous ethanol stream in the contactor. Make-up ethanol from the product recovery zone also passes to the contactor to supply a portion of the first aqueous ethanol stream. A product stream comprising ethanol is recovered from the ethanol recovery zone.

DETAILED DESCRIPTION OF THE INVENTION

This invention may be broadly used in any syngas fermentation application to improve the efficiency and cost effectiveness of removing $CO_2$ from the syngas. The most readily applicable uses include fermentation where the liquid media will primarily comprise a mixture of water and dilute alcohol. This invention offers the multiple advantages of removing $CO_2$ from syngas as well as other trace contaminants that may be present in the syngas gas stream. The other trace contaminants include sulfur compounds such as COS and $H_2S$ as well as nitrogen containing compounds such as $NH_3$ and HCN. This invention does this in a highly integrated manner that utilizes the internal process streams containing alcohol in a manner completely compatible with the production of the alcohol from the syngas. Moreover the invention accomplishes the $CO_2$ and trace contaminant removal with minimal additional vessels or equipment to the process and can provide an enriched alcohol stream for supply to an alcohol recovery section.

Figure 1:
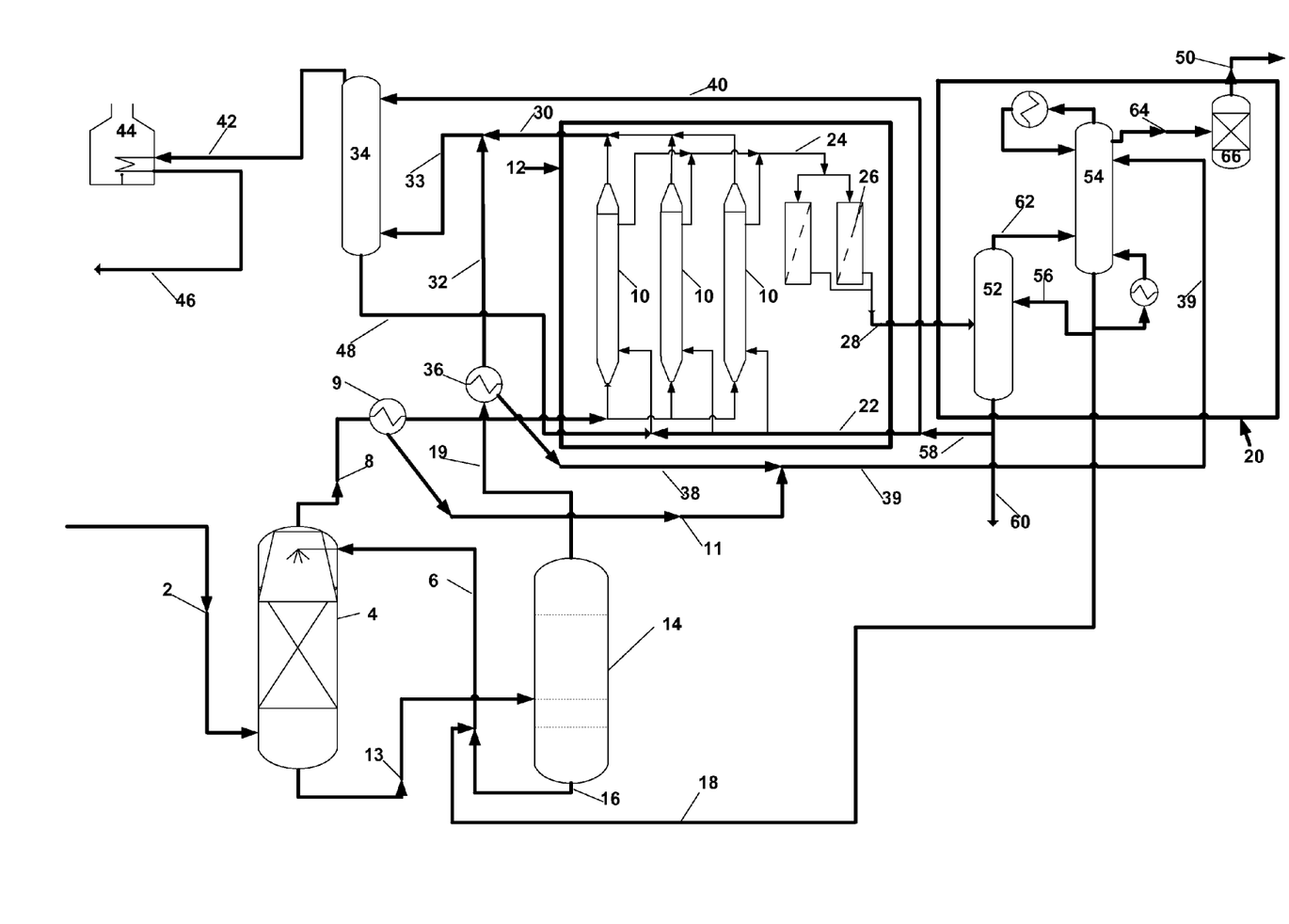
FIG. 1 is a process flow diagram showing the piping and major equipment arranged for the practicing one form of this invention.

A general understanding of the invention and its application is most readily seen in FIG. 1. FIG. 1 shows an overall flow scheme for the process of the invention beginning with an input of synthesis gas to the overall flow scheme depicted in Figure. FIG. 1 omits minor equipment such as pumps, compressors, valves, instruments and other devices the placement of which and operation thereof are well known to those practiced in chemical engineering. The process and operation of FIG. 1 will be described in the context of the recovery and production of ethanol. The process is readily adaptable to making other products such as butanol, isopropanol and acetone.

Referring then to FIG. 1, a syngas stream enters the contactor 4 via a line 2. Contactor 4 in conjunction with a flash vessel 14 removes $CO_2$ from the syngas and recovers $CO_2$ for removal from the process. The syngas typically produced by a gasifier may come from a variety of biomass sources. Any of the aforementioned biomass sources are suitable for producing syngas in this process. The syngas produced thereby will typically contain from 10 to 60 mole % CO, from 10 to 25 mole % $CO_2$ and from 10 to 60 mole % $H_2$. The syngas may also contain $N_2$ as well as trace components such as $H_2S$ and COS. A first aqueous alcohol stream enters the contactor via a line 6 and contains from 30 to 70 mole % ethanol in water. The contactor 4 operates at a pressure of from 1.5 to 10 bars g and a temperature of from 10 to 50° C. Line 8 carries a stream of syngas, reduced in $CO_2$ relative to the entering syngas, overhead and delivers it to a series of bioreactors 10 in a bioreactor zone 12. Passage of the syngas through the contactor 4 reduces the $CO_2$ concentration of the syngas to less than 10 mole % and more typically to less than 5 mole %.

A $CO_2$ enriched liquid stream recovered as liquid phase bottoms from the contactor 4 passes to the flash vessel 14 via a line 13. Flash vessel 14 operates at a temperature of from 10 to 50° C. and a pressure ranging from atmospheric to 0.2 bars g. The flash vessel 14 operates at reduced pressure to release $CO_2$ from the liquid phase. The flashing of the $CO_2$ lifts ethanol overhead with the $CO_2$ along with any other trace contaminant gases such as COS and $H_2S$. A line 19 carries the $CO_2$ effluent overhead to a condenser 36 that produces a $CO_2$ off-gas stream taken by a line 32. The $CO_2$ off-gas stream comprises the $CO_2$ effluent stream 19 less any ethanol removed from the $CO_2$ effluent stream by condenser 36. Line 38 recovers an alcohol enriched stream from the condenser 36. The alcohol enriched stream 38 will have a high ethanol concentration of at least 60 mole % and more typically of at least 70 mole %. The remaining $CO_2$ in the $CO_2$ off gas stream is taken by 32 for removal of the $CO_2$ from the process. The remainder of the mass flow entering flash vessel 14 passes downward in liquid phase to produce a bottoms liquid that provides a second aqueous ethanol stream taken by line 16. Line 16 receives make-up alcohol from a line 18 that together provide the first aqueous ethanol stream that line 6 carries into contactor 4. The make-up alcohol can come from a variety of locations, preferably from a hereinafter described product recovery section 20 that recovers alcohol from the bioreactor zone 12.

The $CO_2$ reduced syngas stream carried by line 8 may optionally undergo condensing to recover a high concentration ethanol stream. FIG. 1 shows the arrangement with CO2 reduced syngas in line 8 passing through a condenser 9 that recovers an ethanol stream carried by a line 11. In the case of a process for producing ethanol, line 11 may comprise ethanol at a concentration of greater than 60 mole % and more typically greater than 70 mole %. The recovered ethanol will usually go directly to product recovery section 20.

Condensed ethanol from line 38 passes to product recovery zone 20. When condenser 9 recovers ethanol from the contactor overhead in line 8, line 39 combines enriched ethanol from both lines 11 and 38 for delivery to zone 20. The amount of ethanol carried by line 39 can equal about 4 to 10% percent of the total ethanol produced by the process. Again when condenser 9 recovers ethanol from the contactor overhead in line 8, the $CO_2$ reduced feed gas stream will pass to the bioreactors 10 of bioreactor zone 12 as the $CO_2$ reduced feed off gas stream.

Bioreactor zone 12 contacts the reduced $CO_2$ syngas from line 8 with microorganisms in the bioreactors 10. Bioconversions of CO and $H_2/CO_2$ to acetic acid, n-butanol, butyric acid, ethanol and other products using microorganisms are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO. This will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid and *Clostridium autoethanogenum* sp. nov., an anaerobic bacterium that produces ethanol from carbon monoxide. Jamal Abrini, Henry Naveau, Edmond-Jacques Nyns, Arch Microbiol., 1994, 345-351; Archives of Microbiology 1994, 161: 345-351. All of these references are incorporated herein in their entirety.

The syngas components undergo conversion in the bioreaction zone 12 by contact with the microorganisms. Many known devices and equipment can effect gas transfer for contacting microorganisms with syngas in a fermentation zone. Any suitable bioreactor apparatus configuration for initial conversion of the syngas to bio-chemicals can be used in the fermentation zone. These systems all keep the microorganisms supplied with liquid from a fermentation broth. Similar devices and equipment for gas-liquid contacting are also known from waste treatment applications.

This invention can apply to any type of bioreactor for producing alcohol from syngas. A typical bioreactor will retain microorganisms suspended in a fermentation broth. Specific types of these bioreactors include bubble column bioreactors and stirred tank bioreactors. These types of reactors will usually operate at atmospheric pressure but can operate over a wide range of pressure conditions. Obtaining good gas dispersion to promote mass transfer of the CO and $H_2$ into the fermentation broth for uptake by the microorganisms is critical to the successful operation of these types of reactors. Many of these conventional bioreactors and systems use agitators with specialized blades or configurations.

In certain types of bioreactors such as gas lift or fluidized beds, liquids or gases are circulated via contacting devices. Particularly suitable bioreactors retain the microorganisms in the form of a biofilm on a substrate surrounded by a fermentation broth. Such substrates include free floating media as described in US 2009/0035848 A1 (filed Aug. 3, 2007) the content of which is hereby incorporated by reference. To get high yields and high production rates the cell concentrations in the bioreactor need to be high and this requires some form of cell recycle or retention. Conventional ways to achieve high cell retention includes filtration of the fermentation broth through microporous or nonporous membranes, returning the cells and then purging the excess.

Cell retention by formation of biofilms or biolayers is a very good and often inexpensive way to increase the density of microorganisms in bioreactors. Formation of biofilms or biolayers requires a solid matrix with large surface area for the microorganisms to colonize and form a biofilm that contains the metabolizing microorganisms in a matrix of biopolymers that the microorganisms generate. Trickle bed and some fluidized bed bioreactors make use of biofilms to retain microorganisms on solid surfaces while providing dissolved gases in the liquid which flows past the solid matrix.

Membranes constitute a class of useful substrates for retaining cells of microorganisms in biofilms or biolayers to obtain the benefits of increased microorganisms density in bioreactors. The membrane offers a solid matrix with a large surface area for an activated surface comprising the microorganisms that colonize and form a biofilm or biolayer to contain the metabolizing microorganisms in a matrix of biopolymers that the cells generate. These systems use microporous membranes or non-porous membranes or membranes having similar properties that transfer (dissolve) gases into liquids while concurrently serving as the support upon which the fermenting microorganisms grow in a concentrated layer. The membrane will also provide a phase separation between the syngas on one side of the membrane and the fermentation broth on the other side of the membrane. Membrane type bioreactors can operate over a wide range of operating conditions including feed gas pressure is in the range of atmospheric to 70 barsg, preferably 0.3 to 30 barsg, and most preferably 0.7 to 15 barsg.

US 2008/0305539 A1 (filed Jul. 23, 2007) (the contents of which are hereby incorporated by reference) discloses the biolayer type of membrane bioreactor. These references describe a membrane based bioreactor wherein anaerobic bacteria that have the ability to convert syngas to ethanol or other liquids have formed biofilms on the surface of hydrophobic membranes. The biolayer can form on the side of the membrane that is closest to the liquid phase such that the syngas feed crosses the membrane from the gas phase side to the biofilm on the surface of the membrane's liquid phase side. In these systems the gas typically flows through a porous region of a hydrophobic membrane and then reaches the hydrophilic biofilm. Such a bioreactor system has been able to directly convert the primary components of synthesis gas, CO, and $H_2/CO_2$ to ethanol and other liquid products such as butanol, hexanol acetic acid, and butyric acid. It is also possible to have the biofilm supported on the side of the membrane that is closest to the gas phase such that the syngas directly contacts the biofilm and the liquid phase crosses the membrane from the liquid phase side and into contact with the biofilm.

Numerous membrane composition and systems are available to serve as substrates for the biofilm. Hollow fiber membrane configurations are particularly useful. Suitable hydrophobic microporous hollow fiber membranes have been used for degassing applications to remove oxygen, carbon dioxide, and other gases from water and other liquids. An example of commercial membrane modules for such applications is the Liqui-Cel® membrane contactor from Membrana (Charlotte, N.C.), containing the polypropylene (PP) X40 or X50 hollow fibers. CELGARD® microporous PP hollow fiber membrane, containing the X30 fibers, is also available from Membrana for oxygenation applications. Liqui-Cel® membrane modules suitable for large scale bindustrial applications have large membrane surface areas (e.g., 220 $m^2$ active membrane surface area for Liqui-Cel® Industrial 14×28)

As opposed to the biofilm type system, a biolayer type of bioreactor will retain microorganisms in or about a porous membrane layer that is closest to the gas phase side of the membrane such that the syngas has direct contact with the microorganism and the liquid crosses the membrane from the membrane's liquid phase side. US 20090215163 A1 (filed Feb. 22, 2008) (the contents of which are hereby incorporated by reference) discloses this type of bioreactor. The biolayer constitutes a membrane structure that provides pores to promote and control the growth of microorganism colonies therein while also exposing a surface over which to directly feed the microorganisms with syngas. Simultaneously another layer of the membrane having less permeability than the biolayer, herein referred to as a hydration layer, permeates liquid from the opposite side of the membrane that contacts the gas phase. In a normal operating mode for a biolayer system, liquid does not permeate past the biolayer or the membrane's liquid phase side. The liquid products produced in the biolayer on the membrane's gas contact side pass through the membrane and into a liquid stream that recovers the desired liquid products while also supplying nutrients to the biolayer in the reverse direction of liquid product flow.

In the biolayer operation the gas side pressure is normally slightly higher than the liquid pressure to prevent convective liquid flow from the hydration layer (liquid) side to the open surface (gas) of the gas contacting side. The higher pressure also avoids formation of a liquid layer at the cell/gas interface, which would impede gas transfer to the cells. U.S. Ser. No. 12/258,193 filed Oct. 24, 2008 (the contents of which are hereby incorporated reference) disclose specific methods of operating biolayer membrane systems to improve product and nutrient interchange by regular laving of the liquid phase in the membrane and flushing the biolayer by periodic purging of liquid onto the membrane's gas phase surface.

Asymmetric membranes provide a highly useful support element for the biolayer type bioreactor. Asymmetric membranes are known for use in a variety of membrane separations processes such as ultra and nano filtration. Asymmetric membranes are typically hydrophilic and have a relatively tight semi permeable "skin" layer on one side supported on a porous polymer layer. U.S. Pat. Nos. 4,442,206 and 4,440,853 show the use of the polymer layer in an asymmetric membrane to immobilize microorganisms for certain biological processes that use soluble carbon sources. US 20090215163 A1 discloses the use of asymmetric membranes to produce alcohols from syngas in a bioreactor that retains microorganisms as a biolayer in or about the surface of a membrane.

Particularly suitable forms of asymmetric membranes are porous membranes with a tight (i.e., having small pores) thin "skin" on one surface of the membrane that provides the hydration layer and a relatively open support structure underneath the skin that provides the biolayer and defines the biopores. The skin will typically comprise a semi-permeable layer having a thickness of from 0.5 to 10 μm. The skinned asymmetric membrane can include an "integrally skinned" membrane prepared by using phase inversion of one polymer or a composite membrane, where a thin layer of a certain material is formed on top of a porous sublayer of a same or different material. General descriptions of asymmetric membranes and methods of their preparation can be found in the literature (e.g., M. Cheryn, *Ultrafiltration and Microfiltration Handbook*, Technomics Publishing Company, Lancaster, Pa., 1998; and M. Mulder, *Basic Principles of Membrane Technology*, $2^{nd}$ *Edition*, Kluwer Academic Publishers, Norwell, Mass., 1996)

Hollow fiber membrane modules containing asymmetric ultrafiltration membranes are commercially available from a number of membrane manufacturers. For example, the Kros-Flo® Max Module Model KM5S-800-01N from Spectrum Laboratories (Rancho Dominguez, Calif.) has 22.0 $m^2$ membrane surface area of asymmetric polysufone hollow fiber membranes with 0.5 mm fiber inner diameter, a tight skin on the lumen side, and a pore rating of 50 kDa. ROMICON® polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 $m^2$ total membrane surface area.

Membranes of the various geometries and compositions described above may be used in arrangements of unitary arrays or assemblies of varied composition in the process of this invention. Any suitable technique can be used to collect and provide the necessary assembly of individual membrane elements. In such membranes the gas and liquid must be circulated into direct and intimate contact with opposing surface of the membrane. Liquid is passed in the liquid side of the membranes via pumping, stirring, or similar means to remove the alcohol, organic acid and other soluble products formed; the products are recovered via a variety of suitable methods. Membranes when arranged in modules provide a large surface area for retention of a biofilm or biolayer particularly when the membranes are in the form of hollow fibers. A number of the membrane modules can be located in a closed membrane vessel so that a very large total membrane surface area can be achieved with a small number of membrane vessels, simplifying plant design and reducing costs.

The bioreactors 10 of FIG. 1 comprise fermentation vessels. Each fermentation vessel receives fermentation liquid from product recovery section 20 via a line 22. Line 8 distributes the reduced $CO_2$ syngas to each of the bioreactors 10. The microorganisms convert the syngas components of $CO_2$ and $H_2$, and CO into ethanol as it passes through the bioreactors 10. Line 24 withdraws a bioreactor effluent stream from each of the bioreactors 10 and delivers it to a microfiltration system 26. Microfiltration system 26 removes cells and cell debris from bioreactor effluent stream ahead of its entry into the product recovery section 20 via line 28. Generation of ethanol by the microorganisms in the bioreactors 10 depletes the CO and $H_2$ from the syngas and produces a tail gas stream consisting of $CO_2$, ethanol and residual gases such as $CH_4$, $H_2S$ and other trace contaminants. Line 30 withdraws the tail gas stream from the bioconversion zone 12.

The tail gas stream from the bioreactors 30 along with a $CO_2$ off-gas stream 32 undergo scrubbing to recover the ethanol contained therein. Line 33 combines a $CO_2$ off-gas stream 32 with the tail gas stream 30 to deliver a combined $CO_2$ stream to scrubber 34.

Scrubbing of the combined tail gas and $CO_2$ off gas in scrubber 34 produces a tail gas scrubber liquid and scrubbed $CO_2$ stream. The product recovery section 20 delivers recycle fermentation liquid to the scrubber 34 via a line 40. Line 42 carries the scrubbed $CO_2$ stream that also contains the residual unconverted gases, $CH_4$, $N_2$, and small amounts of CO and $H_2$ to a thermal oxidizer 44 that produces steam taken via line 46 for use in supplying plant energy requirements. Line 48 returns the tail gas scrubber liquid as additional fermentation liquid to the bioreactor zone 12 either directly to line 22 via line 48 as depicted in FIG. 1 or, depending on the ethanol concentration, via a delivery point in the product recovery section 20.

The product recovery section 20 is highly integrated with the rest of the process to receive ethanol containing streams and deliver fermentation liquid and ethanol containing streams to the bioreactor zone 12, the scrubbing section and the contacting section. Ethanol containing liquid recovered from the bioreactor zone 12 undergoes separation in the product recovery section 20 to recover liquid products. The product recovery section removes the desirable product from liquid, while leaving substantial amounts of water and residual nutrients in the treated stream for return to the bioreactor zone 12 as needed. Any additional nutrient feed may be added to the fermentation liquid at a suitable location (not shown).

Product recovery section 20 receives the primary input of ethanol via a line 28 and delivers an ethanol product stream via line 50. The primary ethanol input from line 28 will contain ethanol at a low concentration that usually ranges from 1 to 6 wt % and more typically ranges from 3 to 6 wt %. A stripper column 52 receives the dilute ethanol stream from line 28. A portion of a net bottoms stream taken by line 56 from a rectification column 54 enters an upper portion of the stripper column. Stripping column 52 produces a bottoms stream 58 and a stripper overhead stream 62. Line 60 removes a purge stream from the stripper bottoms stream 58 and the remainder of stream 58 supplies fermentation liquid to the scrubber 34 via line 40 and to the bioreactor zone via line 22. The stripper overhead stream passes to the rectification column 54 via line 62. A condenser (not shown) may be added provide liquid reflux back to stripper column 52. Line 39 inputs the ethanol enriched stream into the rectification column at a location above the input of line 62. The alcohol enriched stream from line 39 will typically contain over 80 wt % ethanol and may have an ethanol concentration in a range of from 70 to 95 wt %. This ethanol purity may exceed that of the stripping column overhead stream that is typically in a range of from 40 to 70 wt % ethanol. Therefore, when the purity is sufficiently high, ethanol from line 39 can enter the rectification column 54 directly at a suitable tray location. Rectification column 54 will typically deliver a rectified stream via a line 64 to a drying zone 66. Drying zone 66 dehydrates the rectified stream to produce ethanol product stream 50 having an ethanol concentration of at least 99.5 wt % ethanol.

FIG. 1 depicts the make-up liquid for the first aqueous ethanol stream 6 taken by line 18 from rectification bottoms carried in line 56. The typical ethanol concentration for the stream 56 is in a range of from 50 to 80 wt % ethanol. The relative concentration of ethanol in the make-up will determine the concentration of ethanol in the first aqueous ethanol stream and ultimately the ethanol concentration in the contactor 4. The ethanol concentration in the contactor may be adjusted as desired by taking make-up ethanol from other streams with different concentrations or from a combination of different locations. For example, make-up ethanol and water mixtures may be obtained from the overhead of the rectification column via line 56, the alcohol enriched stream via line 38 or directly from the rectification column.

EXAMPLES

The following examples are provided from experimental data and calculations from correlations and represent the expected performance of the method in particular applications as described.

Example 1

Woody biomass from a typical coniferous wood is gasified in a plasma gasifier with oxygen to produce syngas. This gas is cooled to around 40° C. and compressed to a pressure of 3.1 barsg. The typical gas composition of the primary components (in mole fraction) is:

| | |
|---|---|
| CO | 0.5853 |
| H2 | 0.2640 |
| CO2 | 0.1326 |
| H2O | 0.0181 |
| total | 1.0000 |

This gas is fed to a gas-liquid scrubber where the scrubber liquid is a mixture of (50-50 mole %) of ethanol and water (approximately 70 wt % ethanol and 30 wt % water). The scrubbed gas composition of the primary components (in mole fraction) is:

| | |
|---|---|
| CO | 0.6357 |
| H2 | 0.2868 |
| CO2 | 0.0578 |
| H2O | 0.0197 |
| total | 1.0000 |

A comparison of the scrubbed gas with the unscrubbed gas shows a preferential removal of $CO_2$ with very little loss of CO or $H_2$. This gas is then ready for feeding to the bioreactor(s) for conversion of the CO, and $H_2/CO_2$ to ethanol and other liquid products in an arrangement such as the one shown in FIG. 1.

The scrubber liquid moves next to a flash chamber operated at 0.10 barsg and 40° C. The flash chamber removes the $CO_2$ by flashing it from the liquid. The liquid from the flash chamber returns to the scrubber along with any make-up ethanol and water required to replace the portion of the scrubber liquid carried overhead with the flash gas. The flash gas composition is:

| Flash Gas Composition | mole fraction | mass fraction |
|---|---|---|
| $CO_2$ | 0.8515 | 0.8825 |
| CO | 0.0251 | 0.0165 |
| $H_2$ | 0.0105 | 0.0005 |
| Water | 0.0331 | 0.0140 |
| Ethanol | 0.0798 | 0.0865 |
| Total | 1.0000 | 1.0000 |

In comparison with the scrubber gas, the flash gas composition shows that the ethanol to water ratio is increased in the flashed gas to a mole ratio of 70.6-29.4 (mole %) or approximately 86 wt % ethanol and 14 wt % water. This flash gas can be cooled to partially condense the enriched ethanol. When cooled to an average condenser temperature of 25° C. about 60% of the liquid is condensed and the ethanol water mole ratio in the condensed liquid is 70.4-29.6 (mole %) or approximately 86% ethanol and 14% water.

The example shows that this process can substantially remove the $CO_2$ from the syngas without any major loss of CO and $H_2$ while at the same time enhancing the separation of ethanol from water.

Another very beneficial feature of this invention comes from calculating the mass rate of the liquid circulation for the scrubber liquid. A comparison of the scrubber liquid circulation with alcohol and water mixture shows a substantial (5 fold) reduction of the liquid circulation that is required when compared to water alone. For this example with the syngas composition and operating conditions as described above treatment of 45,600 lb/hr of feed syngas would require a circulation rate of approximately 38,000 gallons per minute (gpm) if only water is used. When the 50:50 mole % ethanol: water mixture is used the circulation rate required is approximately 7700 gpm. This substantial reduction in liquid volume enables a major reduction in equipment and capital and operating costs.

Example 2

Woody biomass from typical coniferous wood is again gasified in a fluidized bed gasifier with oxygen. This time the gas is cooled to around 40 C at a pressure of 6.9 barsg and the gas recovered from this operation has the following typical composition of the primary components (in mole fraction):

| | |
|---|---|
| CO | 0.4284 |
| H2 | 0.3791 |
| CO2 | 0.1831 |
| H2O | 0.0094 |
| total | 1.0000 |

This gas again enters a gas-liquid scrubber where the scrubber liquid is a mixture of (50-50 mole %) of ethanol and water (approximately 70 wt % ethanol and 30 wt % water). The scrubbed gas composition of the primary components (in mole fraction) is:

| | |
|---|---|
| CO | 0.4948 |
| H2 | 0.4380 |
| CO2 | 0.0563 |
| H2O | 0.0109 |
| total | 1.0000 |

A comparison of the scrubbed gas with the unscrubbed gas again shows a preferential removal of $CO_2$ with very little loss of CO or $H_2$. This gas is again ready for feeding to the bioreactor(s) for conversion of the CO, and $H_2/CO_2$ to ethanol and other liquid products in an arrangement such as the one shown in FIG. 1.

The scrubber liquid moves again to a flash chamber operated at 0.10 barsg and 40° C. The flash chamber removes the $CO_2$ by flashing it from the liquid. The liquid from the flash zone returns to the scrubber along with any make-up ethanol and water required to replace the portion of the scrubber liquid carried overhead with the flash gas. The flash gas composition is:

| Flash Gas Composition | mole fraction | mass fraction |
|---|---|---|
| $CO_2$ | 0.8626 | 0.8905 |
| CO | 0.0134 | 0.0088 |
| $H_2$ | 0.0111 | 0.0005 |
| Water | 0.0331 | 0.0140 |
| Ethanol | 0.0798 | 0.0861 |
| Total | 1.0000 | 1.0000 |

Again this shows that the ethanol to water ratio is increased in the flashed gas to a mole ratio of 70.7-29.3 (mole %) or approximately 86 wt % ethanol and 14 wt % water. This flash gas can be cooled to partially condense the enriched ethanol. Again when cooled to an average condenser temperature of 25° C. about 60% of the liquid is condensed and the ethanol water mole ratio in the condensed liquid is 70.4-29.6 (mole %) or approximately 86% ethanol and 14% water.

Thus, this Example 2 shows that the process can substantially remove the $CO_2$ from the syngas without any major loss of CO and $H_2$ under a different set of syngas compositions and conditions as compared to Example 1. Again this Example 2 also shows an enhancement in the separation of ethanol from water in the gas coming from the flash step.

Furthermore the very important benefit of the substantial (5 fold) reduction of the required scrubber liquid circulation for ethanol and water versus water alone is again demonstrated with this different set of conditions and syngas composition. With the syngas composition and operating conditions as described for this Example 2 the treatment of 44,000 lb/hr of feed syngas would require a circulation rate of approximately 22,000 gallons per minute (gpm) if only water is used. When the 50:50 mole % ethanol: water is used the circulation rate required is ~4400 gpm. Again this constitutes a major reduction in equipment and capital cost as well as in operating costs.

Example 3

As in Example 1, woody biomass from typical coniferous wood is gasified in a plasma gasifier with oxygen and cooled at conditions of around 40° C. and compressed to a pressure of 3.1 barsg. This time the trace sulfur impurity components of the gas are determined to be (in mole %):

$H_2S$—0.12%, COS—0.012%

The full gas stream again enters a gas-liquid scrubber where the liquid is a mixture of (50-50 mole %) of ethanol and water (approximately 70 wt % ethanol and 30 wt % water). The scrubbed gas composition of the trace sulfur impurities is:

$H_2S$—0.03%, COS<0.001%

This shows that while $CO_2$ is still preferentially removed as shown in the Example 1, the trace impurities are also substantially removed from the gas with very little loss of CO or $H_2$. This gas is again suitable for feeding to the bioreactor(s) for conversion of the CO, and $H_2/CO_2$ to ethanol and other liquid products as shown in the FIG. 1.

The scrubber liquid again moves next to a flash chamber operated at 0.10 barsg and 40° C. The flash chamber removes the $CO_2$ by flashing it from the liquid. The liquid from the flash zone returns to the scrubber along with any make-up ethanol and water required to replace the portion of the scrubber liquid carried overhead with the flash gas. Looking this time at the trace sulfur impurities, approximately 80% of the trace sulfur impurities evolve in the flash gas with the $CO_2$. Following condensation of enriched ethanol this gas containing the $CO_2$ with the trace impurities would undergo purging from the system via a thermal oxidizer as shown in FIG. 1.

What is claimed is:

1. A process for the production of alcohol from a feed gas comprising $CO_2$ and at least one of hydrogen and CO, the process comprising:
   a) contacting a feed gas comprising $CO_2$ and at least one of hydrogen and CO with a first aqueous alcohol stream to absorb $CO_2$ from the feed gas to produce a contacted stream and separating the contacted stream into a $CO_2$ reduced feed gas and a $CO_2$ enriched liquid stream;
   b) passing the $CO_2$ reduced feed gas to a bioreactor for contact therein with microorganisms that convert at least a portion of the hydrogen and $CO_2$, or CO to a bioreactor effluent stream comprising alcohol;
   c) separating the $CO_2$ enriched liquid stream into a gaseous effluent stream comprising $CO_2$ and the alcohol and a second aqueous alcohol stream;
   d) returning at least a portion of the second aqueous alcohol stream to the first aqueous alcohol stream for contact with the feed gas in step a);
   e) recovering alcohol from the bioreactor effluent stream from step b);
   f) introducing a portion of the alcohol from the bioreactor effluent stream of step b) into the first aqueous alcohol stream of step a); and,
   g) condensing the gaseous effluent stream from step c) to produce a $CO_2$ off gas stream and an alcohol enriched stream.

2. The process of claim 1 wherein the bioreactor effluent stream is a liquid comprising at least one of ethanol or butanol.

3. The process of claim 1 wherein the feed gas further comprises $H_2S$ and COS, contact of the feed gas with the first aqueous alcohol stream absorbs $CO_2$, $H_2S$ and COS, and the gaseous effluent stream further comprises $H_2S$ and COS.

4. The process of claim 1 wherein before step b) the $CO_2$ reduced feed gas stream from step a) undergoes separation to produce a $CO_2$ feed off gas stream and a recovered alcohol containing stream and wherein the $CO_2$ feed off gas stream passes to the bioreactor of step b).

5. The process of claim 1 wherein in step c) a flash zone separates the $CO_2$ enriched liquid stream into the gaseous effluent stream and the second aqueous alcohol stream and flashing of the $CO_2$ enriched stream enriches the gaseous effluent stream in alcohol relative to the second aqueous alcohol stream.

6. The process of claim 1 wherein the first aqueous alcohol stream receives make-up alcohol comprising at least a portion of the alcohol enriched stream of step g).

7. The process of claim 1 wherein the first aqueous alcohol stream comprises from 30 to 70 mole % alcohol in water.

8. The process of claim 1 wherein the feed gas contacts the first aqueous alcohol stream at a pressure of from atmospheric to 7 bars g and a temperature of from 25 to 40° C.

9. The process of claim 4 wherein the $CO_2$ feed off gas stream passes to an alcohol scrubber for the recovery of alcohol.

10. The process of claim 1 wherein the bioreactor retains microorganisms comprising a mono-culture or a co-culture of any of *Clostridium ragsdalei, Butyribacterium methylotrophicum, Clostridium ljungdahli* and *Clostridium autoethanogenum*.

11. The process of claim 10 wherein the bioreactor effluent stream is a liquid comprising ethanol.

12. A process for the production of ethanol from a feed gas comprising $CO_2$ and at least one of hydrogen and CO, the process comprising:
   a) contacting a feed gas comprising $CO_2$ and at least one of hydrogen and CO with a first aqueous ethanol stream to absorb $CO_2$ from the feed gas to produce a contacted stream and separating the contacted stream into a $CO_2$ reduced feed gas and a $CO_2$ enriched liquid stream;
   b) passing the $CO_2$ reduced feed gas to a bioreactor for contact therein with microorganisms that convert at least a portion of the hydrogen and $CO_2$, or CO to a bioreactor effluent stream comprising ethanol;
   c) separating the $CO_2$ enriched liquid stream into a $CO_2$ effluent stream and a second aqueous ethanol stream;
   d) recovering ethanol from the $CO_2$ effluent stream from step c) to produce a $CO_2$ off-gas stream and an ethanol enriched stream; and,
   e) adding a portion of the bioreactor effluent stream from step b) to the first aqueous ethanol stream to supply make-up ethanol for contact with the feed gas of step a).

13. The process of claim 12 wherein at least a portion of the bioreactor effluent stream from step b) undergoes separation in a rectification zone to provide an ethanol product stream and at least a portion of the ethanol enriched stream from step d) passes directly to the rectification zone.

14. The process of claim 12 wherein in step c) a flash vessel separates the $CO_2$ enriched stream into the $CO_2$ effluent stream and the second aqueous ethanol stream and the flash vessel enriches the $CO_2$ effluent stream in ethanol relative to the second aqueous ethanol stream.

15. The process of claim 12 wherein the $CO_2$ effluent stream of step c) passes to a condenser and the $CO_2$ off gas stream and the ethanol enriched stream are recovered from the condenser; the ethanol enriched stream of step d) passes directly to a rectification zone, and the rectification zone provides make-up ethanol to the first aqueous alcohol stream to supply ethanol for contact with the feed gas of step a).

16. The process of claim 12 wherein the first aqueous ethanol stream comprises from 30 to 70 mole % ethanol in water.

17. The process of claim 12 wherein the feed gas further comprises $H_2S$ and COS, contact of the feed gas with the first aqueous ethanol stream absorbs $CO_2$, $H_2S$ and COS, and the $CO_2$ off-gas stream further comprises $H_2S$ and COS.

18. A process for the production of ethanol from a feed gas comprising $CO_2$, $H_2$, CO, COS and $H_2S$, the process comprising:
- a) passing the feed gas to a contactor;
- b) passing a first aqueous ethanol stream to the contactor;
- c) absorbing $CO_2$, COS and $H_2S$ from the feed gas in the contactor to produce a $CO_2$ reduced feed gas having a reduced concentration of $CO_2$, $H_2S$ and COS relative to the feed gas and a $CO_2$ enriched stream containing $CO_2$, COS and $H_2S$;
- d) passing the $CO_2$ reduced feed gas to a bioreactor for contact therein with microorganisms that convert at least a portion of the hydrogen and $CO_2$, or CO to a bioreactor effluent stream comprising ethanol;
- e) separating ethanol from the $CO_2$ enriched stream from step c) in a separator to produce a $CO_2$ effluent stream comprising ethanol and $CO_2$ and a second aqueous ethanol stream;
- f) condensing ethanol from the $CO_2$ effluent stream from step e) to produce an ethanol enriched stream and a $CO_2$ off gas stream containing $CO_2$, COS and $H_2S$;
- g) passing at least a portion of the bioreactor effluent stream from step d) and the ethanol enriched stream from step f) to an ethanol recovery zone to produce an ethanol effluent stream having an ethanol concentration of at least 90 wt %;
- h) passing at least a portion of the second aqueous ethanol stream from step e) to the contactor to supply a portion of the first aqueous ethanol stream to step b);
- i) passing make-up ethanol to the contactor to supply a portion of the first aqueous ethanol stream; and
- j) recovering an ethanol product stream from the ethanol recovery zone from step g).

19. The process of claim 18 wherein the first ethanol stream comprises from 30 to 70 mole % ethanol.

20. The process of claim 18 wherein the bioreactor produces a tail gas comprising $CO_2$ and ethanol, the tail gas passes to an ethanol scrubber for the recovery of ethanol, and the $CO_2$ off-gas stream passes to the ethanol scrubber for the recovery of ethanol.

21. The process of claim 18 wherein microorganisms comprises a mono-culture or a co-culture of any of *Clostridium ragsdalei, Butyribacterium methylotrophicum, Clostridium ljungdahli* and *Clostridium autoethanogenum*.

22. The process of claim 18 wherein the $CO_2$ reduced feed gas from step c) prior to step d) passes to a condenser to produce a recovered ethanol containing stream and at least a portion of the recovered ethanol containing stream and at least a portion of the ethanol enriched stream pass to a rectification column in the ethanol recovery zone and wherein the $CO_2$ reduced feed gas that is reduced in ethanol passes to the bioreactor of step d).

* * * * *